(12) United States Patent
Brunelle et al.

(10) Patent No.: US 9,089,415 B2
(45) Date of Patent: Jul. 28, 2015

(54) OBLONG CROSS-SECTIONAL TISSUE FIXATION PEG

(75) Inventors: John Brunelle, Laguna Beach, CA (US); Al Weinstein, East Wayne, NJ (US)

(73) Assignee: Synovis Orthopedic and Woundcare, Inc., Saint Paul, MN (US)

( * ) Notice: Subject to any disclaimer, the term of this patent is extended or adjusted under 35 U.S.C. 154(b) by 1911 days.

(21) Appl. No.: 12/205,340

(22) Filed: Sep. 5, 2008

(65) Prior Publication Data

US 2010/0063541 A1    Mar. 11, 2010

(51) Int. Cl.
*A61B 17/04* (2006.01)
*A61F 2/08* (2006.01)

(52) U.S. Cl.
CPC ............ *A61F 2/0811* (2013.01); *A61B 17/0401* (2013.01); *A61B 2017/0409* (2013.01); *A61B 2017/0412* (2013.01); *A61B 2017/0414* (2013.01); *A61F 2002/0858* (2013.01); *A61F 2002/0888* (2013.01)

(58) Field of Classification Search
CPC .. A61B 17/70; A61B 17/7001; A61B 17/846; A61B 17/7002; A61B 17/0401; A61B 17/0647; A61B 17/0403; A61B 17/0648; A61B 17/0412; A61B 17/0414; A61B 2017/0401; A61B 2017/0647; A61B 2017/0409; A61B 2017/0403; A61B 2017/0412; A61F 2/0811; A61F 2002/0858; A61F 2002/0864; A61F 2002/0888
USPC ................................ 606/151, 232; 623/13.14
See application file for complete search history.

(56) References Cited

U.S. PATENT DOCUMENTS

| | | | |
|---|---|---|---|
| 5,104,405 A | 4/1992 | Nimni | |
| 5,236,431 A * | 8/1993 | Gogolewski et al. | 606/139 |
| 5,447,536 A | 9/1995 | Girardot et al. | |
| 5,472,452 A | 12/1995 | Trott | |
| 5,601,557 A | 2/1997 | Hayhurst | |
| 5,733,339 A | 3/1998 | Girardot et al. | |
| 6,099,530 A | 8/2000 | Simonian et al. | |
| 6,315,564 B1 * | 11/2001 | Levisman | 433/174 |
| 6,436,110 B2 | 8/2002 | Bowman et al. | |
| 6,508,830 B2 | 1/2003 | Steiner | |
| 6,562,044 B1 | 5/2003 | Cooper | |
| 6,635,058 B2 * | 10/2003 | Beyar et al. | 606/232 |

(Continued)

OTHER PUBLICATIONS

*A Defect in the Intramolecular and Intermolecular Cross-linking of Collagen Caused by Penicillamine*, Nimni et al., The Journal of Biological Chemistry,. vol. 243, No. 7, Issue of Apr. 10, pp. 1457-1466, (1968).

(Continued)

*Primary Examiner* — Alexander Orkin
(74) *Attorney, Agent, or Firm* — Daniel G. Stoddard; Bret E. Field; Bozicevic, Field & Francis, LLP

(57) ABSTRACT

Disclosed are fixation devices that can be utilized to approximate and hold a soft tissue in, at, or near a bony insertion site. Disclosed devices can define an oblong cross-section, and can include ribs defining sharp edges on the periphery of one aspect of the cross section that can tightly fix the device to surrounding bone so as to avoid pull out of the device. Devices can also include ribs defining rounded ridges on the periphery of a second, perpendicular aspect of the cross section that can allow soft tissue or a portion of an approximation device, for instance a soft tissue graft or cellular scaffolding material, to be fixed within a bone without damage to the soft tissue.

26 Claims, 13 Drawing Sheets

(56) References Cited

U.S. PATENT DOCUMENTS

| | | |
|---|---|---|
| 6,726,722 B2* | 4/2004 | Walkenhorst et al. ..... 623/17.16 |
| 6,989,034 B2 | 1/2006 | Hammer et al. |
| 7,303,577 B1 | 12/2007 | Dean |
| 7,322,978 B2 | 1/2008 | West, Jr. |
| 7,329,272 B2 | 2/2008 | Burkhart et al. |
| 2003/0032961 A1* | 2/2003 | Pelo et al. ....................... 606/72 |
| 2003/0065390 A1* | 4/2003 | Justin et al. ................ 623/13.14 |
| 2003/0176865 A1* | 9/2003 | Supinski .......................... 606/72 |
| 2007/0156151 A1* | 7/2007 | Guan et al. ...................... 606/72 |
| 2009/0125071 A1* | 5/2009 | Skinlo et al. .................. 606/300 |

OTHER PUBLICATIONS

Nimni et al., J. Biomed. Mater. Res. 21:741-771 (1987).
Woodroof, E. A., J. Bioeng. 2:1 (1978).

\* cited by examiner

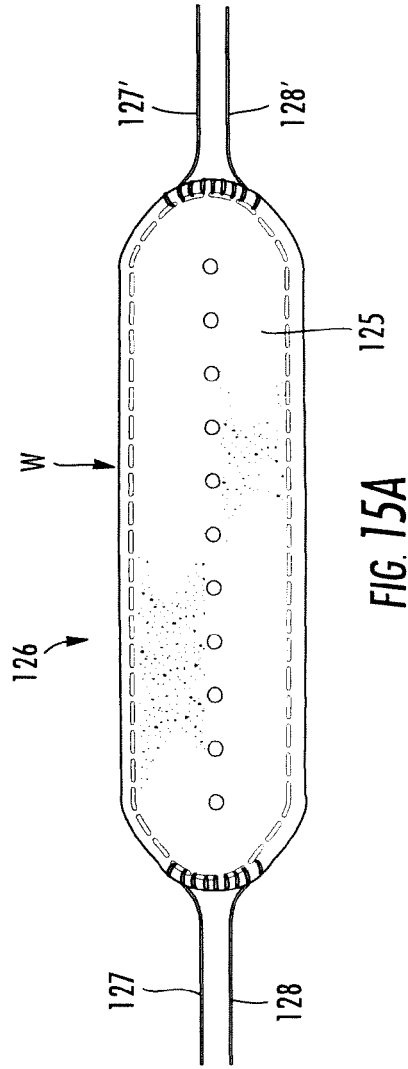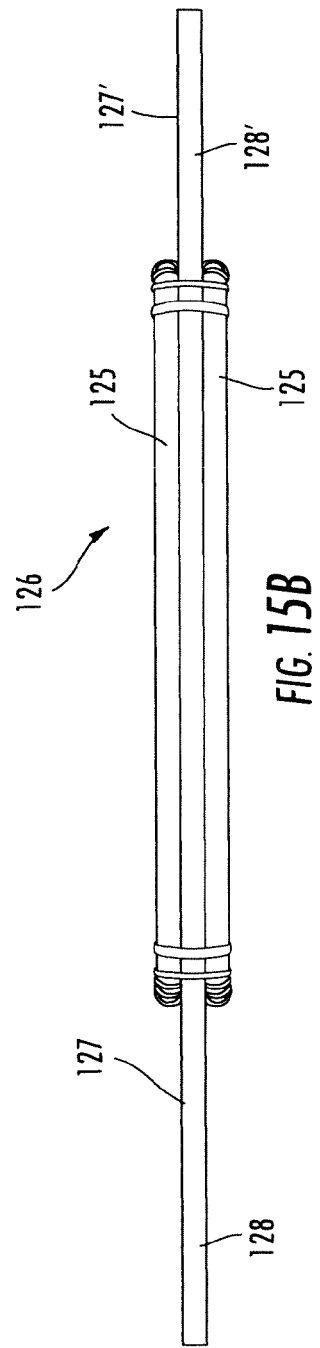

OBLONG CROSS-SECTIONAL TISSUE FIXATION PEG

BACKGROUND

Surgical repair of damaged soft tissue is a procedure that is being carried out with increasing frequency. The most common method for repair of soft tissue damage at or near bone insertion sites involves the approximation of the damaged soft tissue to the insertion site, generally via suture. The suture is then affixed to the insertion site using bone tunnels or a fixation device, e.g., an anchor, which is engaged with the bone. Alternatively, a suture anchor can be first engaged with bone at the soft tissue insertion site and the affixed suture is subsequently used to approximate and secure the damaged soft tissue.

Fixation devices as have been utilized in the past provide certain capabilities. For instance, U.S. Pat. No. 7,329,272 to Burkhart, et al. discloses an interference plug having an outer diameter that is substantially constant and defines a series of ribs and grooves. The device can be utilized to position a graft near a pilot hole and engage within the pilot hole tensioned suture that is attached to the graft. U.S. Pat. No. 7,322,978 to West, Jr. discloses a bone anchor that includes suture attachment sites and continuous threads that extend around the anchor body configured to engage both cortical and cancellous bone tissue. U.S. Pat. No. 6,508,830 to Steiner discloses a suture anchor that includes a cylindrical body portion with an inwardly tapered distal end and a screw thread extending along the body. The device also includes parallel longitudinal grooves cut into the cylindrical body and a transverse suture cavity. In terms of methods, U.S. Pat. No. 5,601,557 to Hayhurst, discloses a method of anchoring and manipulating tissue that includes forming a hole in bone, attaching suture to a member (e.g. an anchor) and securing suture such that the member is lodged into the bone hole and the soft tissue is secured against the bone.

While the above provide improvements in the art, problems still remain. For instance, devices that can provide a high pressure interface with bone, such as through inclusion of sharp ridges or edges, can provide resistance to pull out. However, these devices require special features and knot tying so as to receive suture and to shuttle through and approximate damaged soft tissue to the insertion site. In addition, any direct contact at these high pressure interfaces with soft tissue or an approximation device (e.g., suture) can result in damage, for instance fraying of suture that can compromise the repair. Finally, the above devices and methods are limited to use with suture, and thus cannot be adapted for use with evolving tissue repair constructs such as a surgical mesh or cellular scaffold.

On the other hand, fixation devices that can directly fixate soft tissue within a bone tunnel or slot typically exhibit rounded, atraumatic edges or ridges, usually including insertion with a screw configuration, that are designed to reduce tissue damage. For instance, U.S. Pat. No. 6,099,530 to Simonian, et al. discloses a soft tissue fixation device that includes four channels and four securing members. The four channels include ribs with rounded edges that aid in securing soft tissue in the channels. The four securing members can include a set of wedges oriented toward the distal end of the device that provide an interference fit between the securing members and the wall of the bone tunnel. U.S. Pat. No. 6,562,044 to Cooper describes a multi-component device that includes a first portion including spikes for engaging a graft in a bone tunnel and a second portion, an interference screw having threads, that can be threaded into the bone hole to engage the inner surface of the first portion and an edge of the bone hole to secure the device and the graft in the bone tunnel. These devices rely primarily on compression and friction between the device, the tissue, and the inner bone wall to resist pull out, which is less mechanically desirable than devices that include the direct mechanical interface obtained with devices that include sharper, higher pressure anchoring means. In addition, fixation devices such as those disclosed by Cooper that utilize threaded screw configurations are prone to motion that can cause the soft tissue graft or stump to twist and move from the original placement point.

What are needed in the art are fixation devices that can provide improved mechanical repair of soft tissue injuries and are adaptable to interface with a range of tissue repair constructs and techniques (e.g. tendon stump, suture, and surgical mesh). What are also needed in the art are fixation devices that can provide for both mechanical repair and tissue augmentation in a single step procedure.

SUMMARY

Disclosed in one embodiment is a tissue fixation device. For example, a tissue fixation device can include a proximal end and a distal end and a longitudinal axis between the two. A tissue fixation device can also define an oblong cross section. More specifically, a cross sectional area of a device can include a first aspect and a second aspect that is perpendicular to the first aspect, with the second aspect being shorter than the first aspect such that the cross sectional area is oblong.

Devices as disclosed herein can also include ribs extending from portions of the periphery of the cross section of the body. For instance, a device can include a rib defining a sharp edge that can extend from a portion of the periphery including the terminus of the longer, first aspect of the cross section.

Fixation devices can include a second shaped rib including a rounded ridge, rather than a sharp edge. For instance, a device can include a second rib that defines a rounded ridge that can extend from a portion of the periphery including the terminus of the shorter, second aspect of the cross section.

Disclosed fixation devices can also include a transverse aperture passing from one side to the other. This transverse aperture can be generally perpendicular to the longitudinal axis of the device. Generally, a transverse aperture can be aligned with the shorter, second aspect of the oblong cross section. In addition, a transverse aperture can be located anywhere along the longitudinal axis of the device, or can be closer to the distal end of the device than the proximal end.

Also disclosed are methods for utilizing the fixation devices in repair of soft tissues. For example, a method can include passing a tissue approximation device (e.g., a suture, a suture in conjunction with a woven construct and/or a collagen scaffold, and so forth), a tissue (e.g., an endogenous tissue stump or a tissue graft), or a tissue reinforcement device (e.g. surgical mesh) through a transverse aperture of a device.

A method can also include placing the tissue or tissue approximation device over a particular portion of the fixation device. For instance, the tissue or tissue approximation device can be placed over a portion of a fixation device such that following insertion of the fixation device into a bone hole, the tissue or tissue approximation device can be held between the ribs defining the atraumatic rounded ridges and the surface of the bone hole. In addition, following insertion of a device into a bone hole, sharp edged ribs extending from a portion of the device can be in direct contact with the surface of the bone hole. Accordingly, a device can be tightly held in the bone via the sharp edged ribs and can also hold a tissue or a tissue approximation device in the hole via the round ridged ribs such that they are less susceptible to damage.

A method can also include the fixation of a reinforcing surgical mesh device, such that the portions of the surgical mesh device in contact with the longer first aspect of the disclosed fixation device maintains flatness and thus maintains contact area with tissues surrounding the bone hole.

Further still, a method can include the delivery of collagen (e.g. tendon stump, collagen scaffold) to a bleeding boney insertion site, providing additional vascularity to the repair to aid in healing.

BRIEF DESCRIPTION OF THE FIGURES

A full and enabling disclosure of the present subject matter, including the best mode thereof, to one of ordinary skill in the art, is set forth more particularly in the remainder of the specification, including reference to the accompanying figures, in which:

FIGS. 15A and 15B illustrate a top (FIG. 15A) and side (FIG. 15B) view of one embodiment of an approximation device as may be utilized in conjunction with disclosed fixation devices.

Figure 1:
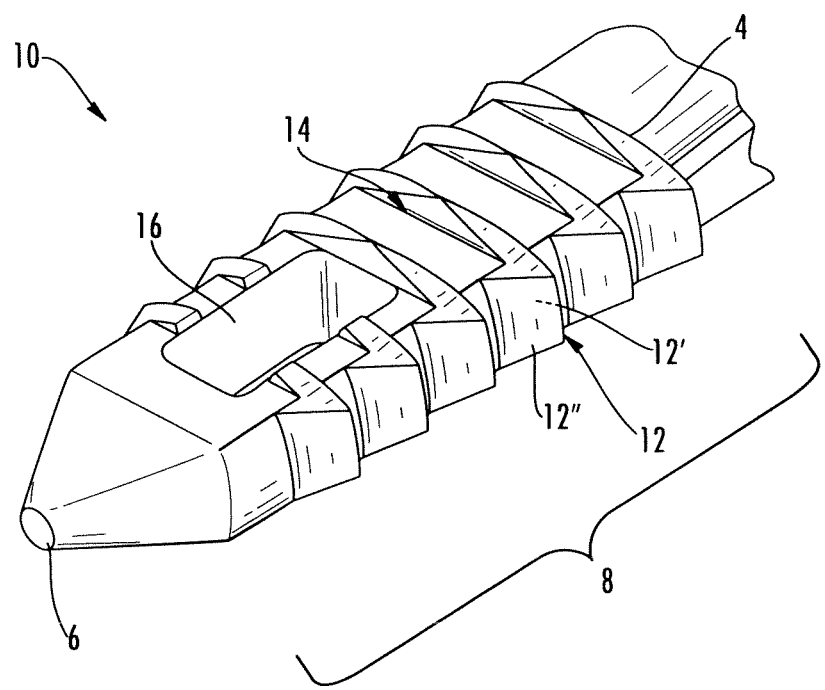
FIG. 1 illustrates a perspective view of one embodiment of a fixation device as disclosed herein.

Repeat use of reference characters in the present specification and drawings is intended to represent the same or analogous features or elements of the present disclosure.

DETAILED DESCRIPTION

Reference will now be made in detail to various embodiments of the disclosed subject matter, one or more examples of which are set forth below. Each embodiment is provided by way of explanation of the disclosed subject matter, not limitation thereof. In fact, it will be apparent to those skilled in the art that various modifications and variations may be made in the present disclosure without departing from the scope or spirit of the subject matter. For instance, features illustrated or described as part of one embodiment, may be used with another embodiment to yield a still further embodiment.

Presently disclosed subject matter is generally directed to a fixation device that can be utilized in one preferred embodiment to approximate and hold a soft tissue at, near, or within a bony insertion site. More specifically, disclosed devices can include features that can tightly fix the device to surrounding bone so as to avoid pull out of the device, and can also include features that can allow endogenous soft tissue or other soft material, for instance a soft tissue graft or cellular scaffolding material, to be fixed within a bone slot or bone hole without damage to the soft tissue.

FIG. 1 illustrates a perspective view of one embodiment of a fixation device 10 as described herein. As can be seen, device 10 has a proximal end 4, a distal end 6, and a main body 8 therebetween.

The main body 8 of device 10 is generally oblong or ovoid in cross-section. That is, the dimensions of the cross section of the main body can be elongated in one aspect in relation to a second aspect perpendicular to the first aspect. Accordingly, the cross sectional area along at least a portion of the longitudinal axis of a device as disclosed herein can be oblong, e.g., ovoid, elliptical, rectangular, and so forth.

In addition, the cross section of device 10 leading to distal end 6 can be shaped so as to aid in proper delivery and insertion of a device 10 into a bone, i.e., into a bone hole or bone slot. For instance, in the illustrated embodiment, distal end 6 can define a relatively small cross-sectional area as compared to the main body 8 of device 10 and can be formed through tapering the cross-sectional area of the main body 8 toward the distal end 6.

Main body 8 of device 10 can include distinct features providing characteristics to the device. For instance, device 10 includes a series of ribs 12 extending from a portion of the periphery of the main body that is on the longer aspect of the cross section, e.g., a portion of the body periphery that is generally centered about the major axis of a cross sectional ellipse. As can be seen, ribs 12 define sharp edges at the edge where two surfaces 12', 12" meet. The sharp edges of ribs 12 can provide a direct, high pressure mechanical interface with bone and as such improve resistance to pull out opposite the direction of insertion.

Figure 2:
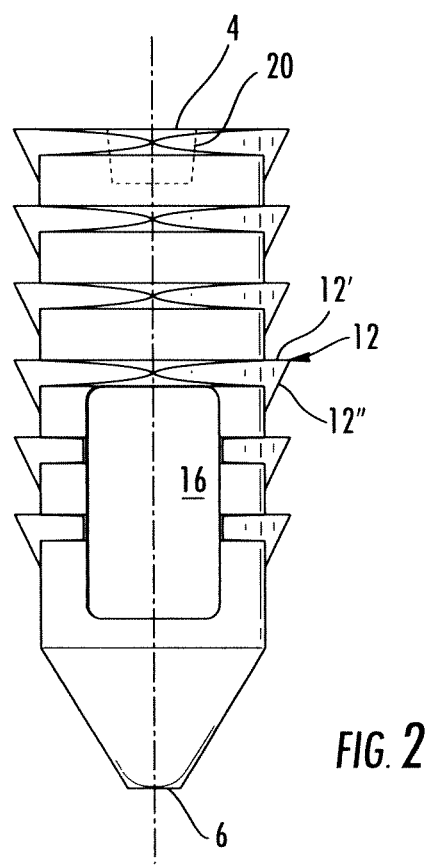
FIG. 2 illustrates a front view of one embodiment of a fixation device as disclosed herein.

FIG. 2 illustrates a front view of device 10. In this particular embodiment ribs 12 extend from the main body 8 in a generally perpendicular direction as compared to the axial direction of device 10. This is not a requirement of the disclosed subject matter, however, and in other embodiments, ribs 12 can extend at an angle from main body 8.

Figure 3:
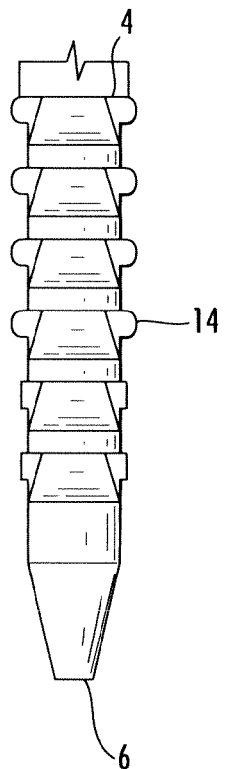
FIG. 3 illustrates a side view of one embodiment of a fixation device as disclosed herein.

Referring again to FIG. 1, device 10 can also include a series of ribs 14, distinct from ribs 12, extending from the main body 8 at a portion of the periphery along the shorter aspect of the cross-section, e.g., that portion of the body periphery including at its approximate center the minor axis of a cross sectional ellipse. Ribs 14 define a rounded ridge, i.e., the terminal ridge of ribs 14 can have a measurable radius of curvature. The rounded ridge aspect of ribs 14 can be clearly seen in FIG. 3, which is a side view of the device 10 of FIG. 1. The rounded ridges of ribs 14 can provide atraumatic contact with soft tissue and/or approximation devices, e.g., suture, within a bone hole or bone slot.

The total number of ribs 12 and ribs 14 included on a device 10 can generally vary according to the overall length of device 10. For instance, device 10 can be of any suitable length, with preferred length generally depending upon specific procedures and locations involved in a procedure. In general, a fixation device 10 can be between about 5 millimeters (mm) and about 30 mm in length, as measured from the proximal end 4 to the distal end 6, though longer or shorter devices may be utilized as well. Accordingly, the number of ribs 12 and ribs 14 to be formed along the length of a device 10 can be determined according to formation techniques, overall length of the device, as well as size of individual ribs 12 and ribs 14. For instance, device 10 can included between about 4 and about 7 ribs in one application, or between about 7 and about 12 ribs in another. Moreover, the number of ribs 12 can be the same as the number of ribs 14 or can be different. Preferred numbers of ribs for any particular embodiment will generally depend upon design requirements. Additionally, the spacing of the ribs along the length of the device can vary according to design requirements. For instance, ribs may be formed closer together or farther apart relative to the overall length of the device. Further, the ribs may be formed with regard to a particular end of the device, for instance the ribs may be concentrated at the proximal end of the device.

In general, a device can include an equal number of ribs 12 on two opposing portions of the device 10 and an equal number of ribs 14 on two opposing portions of the device 10. For instance, in the embodiment illustrated in FIGS. 1-3, device 10 includes six ribs 12 on opposing portions of the device that include the terminus of the major axis of the cross sectional ellipse of main body 8. Device 10 includes six ribs 14 on either opposing portions of the device that includes the terminus of the minor axis of the cross sectional ellipse of main body 8. Equal distribution of ribs 12, 14 on opposing portions of a device can provide a more equal distribution of forces over the device following insertion, but it is not a requirement of disclosed devices.

The sharp edge of any individual rib 12 can be planar with the rounded ridge of an individual rib 14, or can be offset therefrom, as desired. By way of example, in the embodiment illustrated in FIGS. 1-3, the proximal planar aspect of the rounded ridges of ribs 14 are parallel and essentially in line with the proximal planar aspect sharp edges of ribs 12.

Referring again to FIG. 1, ribs 14 near the distal end 6 of device 10 are interrupted by a transverse aperture 16. As can be seen, transverse aperture 16 passes through the device and is generally perpendicular to the longitudinal axis of the device. Transverse aperture 16 can be of any size to allow an approximation device and/or soft tissue to pass through, as is further explained within. For example, transverse aperture 16 can be between about 1 mm and about 6 mm in height and can be between about 1 mm and about 5 mm in width. Transverse aperture 16 can be of any suitable shape including, without limitation, rectangular (as shown), circular, ovoid, triangular, elliptical, etc. Transverse aperture 16 can pass through device 10 such that materials passed through the transverse aperture can exit the aperture and contact a portion of the device including ribs 14 that define rounded ridges. For example, in the illustrated embodiment, ribs 14 defining rounded ridges are on the periphery of the longer portion of the oblong cross section, i.e., they extend from that portion of the periphery that includes the terminus of the shorter aspect of the cross section. Accordingly, the transverse aperture 16 is aligned with this shorter aspect and perpendicular to the longer aspect, so as to pass from a first side of device 10 including ribs 14 to the opposite side of the device 10 also including ribs 14.

Though illustrated as near the distal end 6 of device 10, it should be understood that the location of transverse aperture 16 is not a requirement of disclosed fixation devices. In particular, a transverse aperture can be located anywhere along the longitudinal axis of a fixation device. Additionally, a fixation device as disclosed herein may include a plurality of transverse apertures.

Though illustrated as placed symmetrical about the longitudinal axis of device 10, it should be understood this is not a requirement of disclosed fixation devices. In particular, a transverse aperture can be offset in greater part or entirely to one particular side of the longitudinal axis of a fixation device.

Figure 4:
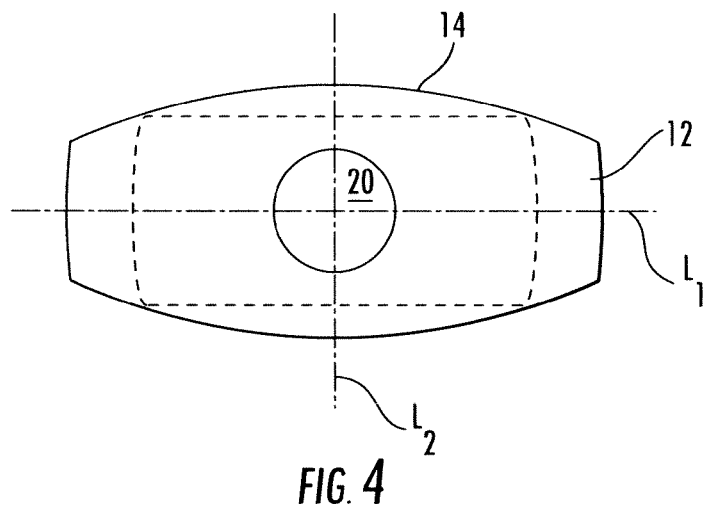
FIG. 4 illustrates a top view of one embodiment of a fixation device as disclosed herein.

FIG. 4 is a top view of device 10. As can be seen, device 10 includes an elliptical cross section including major axis L1 and minor axis L2. As previously mentioned, while the cross sectional area of the main body of a device according to the disclosed subject matter is oblong, it is not necessarily elliptical. Cross sectional areas of devices as disclosed herein can be rectangular or any regular or irregular ovoid shape. Overall cross-sectional dimension of a device 10 can generally vary according to location and utilization, as is known in the art. In general, however, the longer aspect, or major axis, of a device cross section can be between about 2 mm and about 10 mm, and a shorter aspect, or minor axis, of a device cross section can vary between about 1 mm and about 6 mm. However, larger or smaller devices are also encompassed in the present disclosure.

Figure 5:
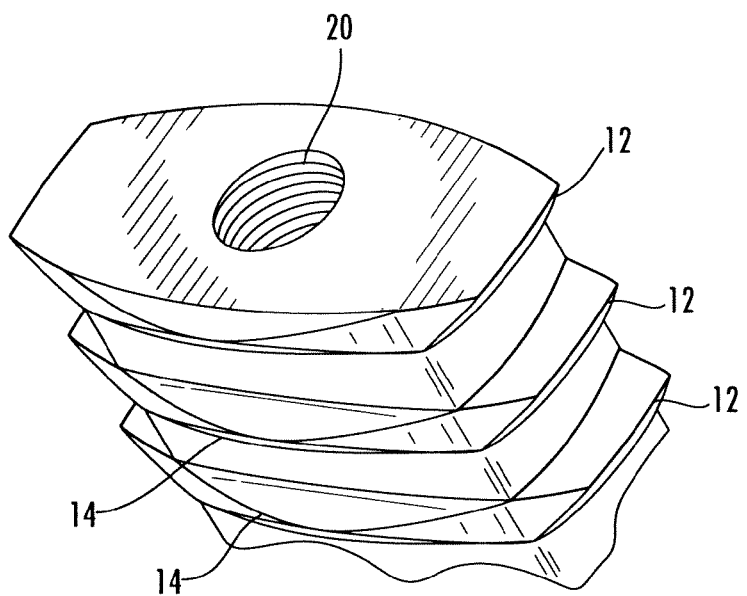
FIG. 5 is a perspective view of one embodiment of a fixation device as disclosed herein including the proximal end portion.

Device 10 can also include an inset 20 defined by proximal end 4 of the device. Inset 20 is configured to interface with a delivery mechanism, for instance a driver, to aid in delivery of device 10 to a bone hole or bone slot. In the illustrated embodiment, and as can be seen in FIG. 5, inset 20 is threaded, so as to interface with the terminal portion of a threaded driver, according to known practices, though this is not a requirement of disclosed devices. Any suitable interface between proximal end 4 of device 10 and a delivery mechanism can be utilized including, without limitation, simple peg/hole interface, specifically shaped interface (e.g., hex-shaped), a multi-dimensional bore/driver interface, and the like. Additionally, delivery mechanism interfaces are not limited to inset configurations. Proximal end 4 can define a protrusion that may insert into a recess in a delivery device, for instance a driver shaft recess.

Sharp edges of ribs 12 and rounded ridges of ribs 14 can generally follow any curvature of the main body of a device 10. Optionally, however, the ribs can follow a different contour. For instance, sharp edges of ribs 12 can be more squared-off and can provide increased contact area at a device/bone interface.

Sharp edges of ribs 12 and rounded ridges of ribs 14 can generally be formed at any depth from the periphery of device 10 depending on application and design requirements. For instance, an increase in the depth of ribs 12 may increase pull out resistance from bone. In general, the depths of ribs 12 and ribs 14 can vary from about 0.25 millimeters to about 2 millimeters, or as required by application.

Figure 6:
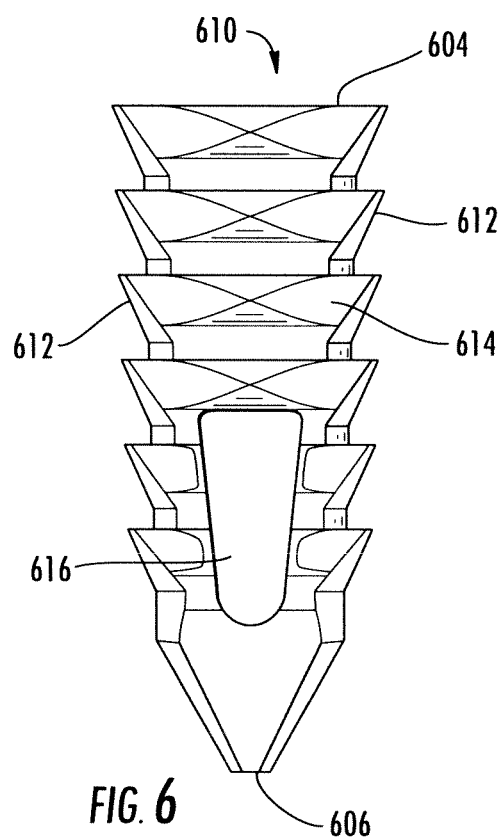
FIG. 6 illustrates another embodiment of a fixation device as disclosed herein.

FIG. 6 illustrates a front view of device 610. The body of device 610 is tapered such that the cross sectional area decreases moving from proximal end 604 to distal end 606 along the central axis. In this particular embodiment, the device 610 includes a first angle of taper from proximal end 604 to the base of transverse aperture 616, and a second angle of taper from the base of transverse aperture 616 to distal end 606. Of course, any combination of taper angles across the longitudinal axis of a device is encompassed herein. Moreover, in this particular embodiment, transverse aperture 616 also defines a tapered edge, but this is not a requirement of the disclosed subject matter.

A taper across all or a portion of the longitudinal axis of the device can be beneficial in assisting insertion into a preformed bone tunnel by effectively reducing the force required for insertion. The taper can be of varying degrees depending in the requirements and specifications of the employed technique and can occur over the entire length of the device, or along any portion therein. Additionally, the taper can be symmetrical or asymmetrical about the central axis and can occur along any plane moving proximal to distal along the central axis of the device. For example, in the illustrated embodiment, device 610 defines a taper with respect to the longitudinal axis along both portions of the device 610 that define sharp ribs 612. In general, this taper angle can be about 1° to about 4° along a particular portion, or as required by application. As to the portions of device 610 that define ribs 614, device 610 can also define a taper with respect to the longitudinal axis, though this taper is not shown in this particular view. Alternatively, those portions of device 610 that define ribs 614 can be generally parallel to the longitudinal axis, while one or both portions of the device that define the sharp ribs 612 can be tapered across the length of the device. Any or all cross sectional portions of device 610 can define a taper along all or a portion of the longitudinal axis of the device.

Figure 7:
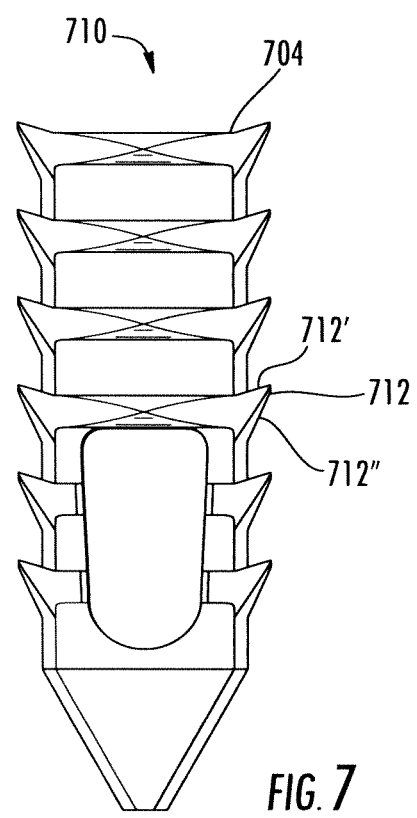
FIG. 7 illustrates another embodiment of a fixation device as disclosed herein.

FIG. 7 illustrates a front view of another fixation device 710. In this particular embodiment, ribs 712 are orientated upwardly toward the proximal end 704 of device 712. In this embodiment, surface 712' of rib 712 can be inclined from perpendicular as compared to the cross section of device 710. Thus, ribs 712 can be oriented in a direction toward proximal end 704 of device 710.

The specific orientation of the sharp edged ribs of the disclosed devices in not critical. For instance, with reference to FIG. 1, ribs 12 are generally planar with regard to the cross section of device 10. However, with reference to FIG. 7, ribs 712 are oriented toward the proximal end 704 of device 710. Similarly, sharp edged ribs could be alternatively oriented toward the distal end of a device, as desired. Additionally, surface 712" can be orientated at different angles in reference to the longitudinal axis. Rib surfaces 712' and 712" can also take different shapes, for example contain specific contours or curvatures defined by a radius.

Figure 8:
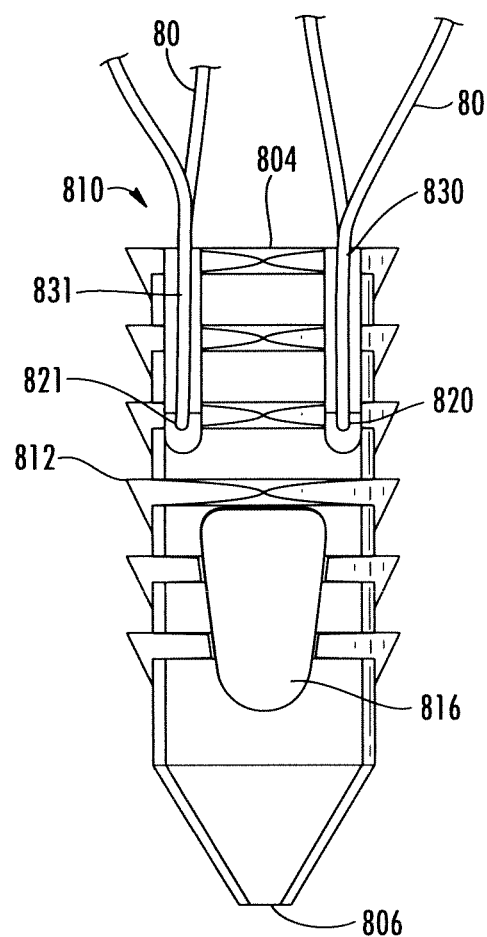
FIG. 8 illustrates another embodiment of a fixation device as disclosed herein.

A device can include additional apertures as desired. For instance, FIG. 8 illustrates a front view of device 810. In this embodiment, device 810 defines transverse suture apertures 820, 821 for receiving suture 80 therethrough. Suture apertures 820, 821 can generally be parallel and aligned with one another. Suture apertures 820, 821 can also be aligned with the shorter aspect of the oblong cross section of device 810 and perpendicular to the longitudinal axis of device 810. A device can include no, one, two or more suture apertures. In addition, suture apertures 820, 821 can be located anywhere along the longitudinal axis of a device 810. For example, suture apertures 820, 821 can be located centrally about the proximal and distal ends 804, 806 of device 810. Similarly, suture apertures 820, 821 can be located anywhere across the longer sides of the oblong cross section, i.e., the terminus of the shorter aspect of the cross section. For example, suture apertures 820, 821 can be placed symmetrically about the longitudinal axis of the device, as in the illustrated embodiment.

Suture apertures 820, 821 can be of a size to allow appropriate suture to pass through, for example, suture apertures 820, 821 can be sized to receive up to a #5 suture. Suture apertures 820, 821 can be of any suitable shape including, without limitation, circular, ovoid, square, etc.

Device 810 also defines grooves 830, 831 that are aligned parallel to the longitudinal axis and perpendicular to the axis of the transverse apertures of the device. Grooves 830, 831 extend from the suture apertures 820, 821, respectively, to the proximal end 804 of device 810. Grooves 830, 831 can be of a depth that can facilitate the sliding of suture relative to the device, and specifically, following the insertion of the device 810 into bone. For example, grooves 820, 821 can facilitate the tying of arthroscopic sliding knots during rotator cuff surgery. Alternately, a suture 80 can be contained within device 810 though an internal channel aligned with the longitudinal axis.

Disclosed fixation devices can be formed from any of a wide variety of biocompatible materials and can be formed from any material or combination of materials that can provide desired physical, chemical, or biological characteristics. For example, devices can be polymeric, metallic, or any other suitable material. Exemplary materials of formation can include, without limitation, polyether ether ketone (PEEK), stainless steel, titanium, polyester, polyoxymethylene (e.g., Delrin®), polysulphones, ultra high molecular weight polyethylene (UHMWPE), absorbable polymers (e.g., polylactic acid, polyglycolic acid, and so forth), reinforced polymers (e.g., fiber reinforced polymer matrices), polymer blends, copolymers, and composite materials.

Fixation devices can be formed according to any suitable formation technique including, without limitation, machining, extrusion, molding, fused deposition modeling, selective laser sintering, stereolithography, and so forth. For example, a polymeric or metal fixation device can be formed through multi-axis machining, according to methods as are generally known to those of ordinary skill in the art. Other machining methods as may be utilized can include, without limitation, lathing, milling, electrical discharge machining (EDM), stamping, and so forth. By way of example, extrusion methods can include multi-phase as well as step extrusion methods, as are generally known. Molding methods as may be utilized can include injection molding, pulltrusion molding, rotomolding, solvent molding, cast molding, compression molding, polymerization molding (i.e., monomers and/or oligomers are polymerized within the mold), and so forth. Of course, multiple formation methods can be utilized in conjunction with one another as well.

Disclosed fixation devices can be provided as sterile or non-sterile devices, depending upon the desired application of a particular device. When considering sterile devices, any sterilization procedures can be utilized as is generally known in the art. For example, disclosed fixation devices can be sterilized by liquid chemical, gas chemical, radiation, or any other sterilization process.

During use, disclosed fixation devices can fixate a soft tissue in, at, or near a bone hole or bone slot. For example, and with reference to FIG. 9, a fixation device 10 can be utilized to fixate a tendon end 32 near a bone hole 24 through utilization of an approximation device 26.

In the illustrated embodiment, an approximation device is similar to those disclosed in pending U.S. patent application having Ser. No. 11/777,733 to Brunelle, et al., which is incorporated herein by reference. For example, an approximation device can include a cellular scaffold 25 and an elongated member 28 affixed to the scaffold. The cellular scaffold 25 can have a structure and be formed of a material so as to allow cellular ingrowth thereto. For instance, it can be formed of natural tissue or can be a synthetic construct. In one preferred embodiment a scaffold can contain collagen. For example, a scaffold 25 can contain crosslinked collagen.

As utilized herein, the term 'scaffold' and 'cellular scaffold' are intended to be interchangeable and can generally refer to biocompatible materials that can facilitate cellular growth and development when located in proximity to living cells. Scaffold materials encompassed herein include those designed for in vivo, ex vivo, and/or in vitro use. In general, scaffold materials can describe a physical structure that can allow cellular ingrowth to the scaffold. For example, a scaffold can include macro- and/or microporosity that can allow cellular propagation throughout all or a portion of the scaffold. In one embodiment, a scaffold can include a matrix with a mesh size, $\xi$, or a pore size, $\rho$ that can allow cellular propagation and/or ingrowth throughout the matrix.

A scaffold 25 can include one or more materials that encourage the growth and development of a cellular construct. For instance, a scaffold can include one or more synthetic or natural biocompatible polymers that have been shown to promote wound healing. Biocompatible synthetic polymers as may be utilized in forming a scaffold can include, e.g., polyurethanes, polyesters, polyethylenes, silicones, polyglycolic acid (PGA), polylactic acid (PLA), copolymers of lactic and glycolic acids (PLGA), polyanhydrides, polyorthoesters, and the like. A scaffold can include one or more natural polymers including, e.g., chitosan, glycosaminoglycans, and collagen.

In one embodiment, a scaffold 25 can include or be formed entirely of a hydrogel matrix. Hydrogel scaffolds are known in the art and are generally defined to include polymeric matrices that can be highly hydrated while maintaining structural stability. Suitable hydrogel scaffolds can include non-crosslinked and crosslinked hydrogels. In addition, crosslinked hydrogel scaffolds can optionally include hydrolyzable portions, such that the scaffold can be degradable when utilized in an aqueous environment. For example, in one embodiment, a scaffold can include a cross-linked hydrogel including a hydrolyzable cross-linking agent, such as polylactic acid, and can be degradable in an aqueous environment.

Hydrogel scaffolds can include natural polymers such as glycosaminoglycans, polysaccharides, proteins, and the like, as well as synthetic polymers, as are generally known in the art. A non-limiting list of polymeric materials that can be utilized in forming hydrogel scaffolds can include dextran, hyaluronic acid, chitin, heparin, collagen, elastin, keratin, albumin, polymers and copolymers of lactic acid, glycolic acid, carboxymethyl cellulose, polyacrylates, polymethacrylates, epoxides, silicones, polyols such as polypropylene glycol, polyvinyl alcohol and polyethylene glycol and their derivatives, alginates such as sodium alginate or crosslinked alginate gum, polycaprolactone, polyanhydride, pectin, gelatin, crosslinked proteins peptides and polysaccharides, and the like.

In one preferred embodiment, a scaffold 25 can contain collagen. Collagen is the most abundant fibrous structural protein found in mammals and has been shown to exhibit many desirable qualities in scaffolding materials. For example, in addition to good bioaffinity and histocompatibility, wound healing cells such as fibroblasts have been shown to have good affinity for collagen, and the presence of collagen in a scaffold can encourage and promote cell growth and differentiation of the tissues/cells associated with the scaffold.

Collagen encompassed can include any collagen type or combination of collagen types. For instance, a collagen-containing scaffold can include any one or combination of the currently known 28 types of collagen. Typically, a collagen-containing scaffold can include at least some type I and/or type II collagen, but this is merely due to the fact that types I and II collagen are the most abundant types of collagen, and it should be understood that the presence of either of these types is not a requirement in a collagen-containing scaffold.

A collagen-containing scaffold can be derived of any suitable collagen source and can be formed according to any suitable method as is understood by one of ordinary skill in the art. For example, a collagen-based scaffold can include natural collagen-containing tissues that can be allograft, autograft, and/or xenograft tissues. Natural collagen-containing tissues that can be used to form a scaffold can include, without limitation, soft tissues including ligament, tendon, muscle, dura, pericardium, fascia, peritoneum, and the like and can be derived from any host source (human, equine, porcine, bovine, etc.).

Collagen-containing materials can be processed according to any suitable methods during a scaffold preparation process. For instance, a collagen-containing scaffold can be derived from reconstituted collagen. The capability of utilizing reconstituted collagen to form a scaffolding material was first published by Bell, et al. in 1979 (Proc. Natn. Acad. Sci. USA, 76, 1274-1278, incorporated herein by reference). In general, methods for forming scaffolds from reconstituted collagen include extraction and purification of collagen(s) from connective tissues by solubilization that can be acidic, alkaline, neutral and/or enzymatic in nature. The extracted collagen can be broken down to monomeric and/or oligomeric level and stored as a powder or liquid. Upon rehydration, a solution can form that can be molded and crosslinked via chemical or physical methods to form a scaffold.

A scaffold may be processed as desired prior to forming a composite implant. For instance, a natural or reconstituted tissue can be stabilized through crosslinking. Generally, a stabilization process operates by blocking reactive molecules on the surface of and within the scaffold, thereby rendering it substantially non-antigenic and suitable for implantation. In 1968, Nimni et al. demonstrated that collagenous materials can be stabilized by treating them with aldehydes. (Nimni et al., J. Biol. Chem. 243:1457-1466 (1968).) Later, various aldehydes were tested and glutaraldehyde was shown to be capable of retarding degeneration of collagenous tissue. (Nimni et al., J. Biomed. Mater. Res. 21:741-771 (1987); Woodroof, E. A., J. Bioeng. 2:1 (1978).) Thus, according to one embodiment, a glutaraldehyde stabilization process as is generally known in the art may be utilized in forming a scaffold (see, e.g., U.S. Pat. No. 5,104,405 to Nimni, which is incorporated herein by reference).

A glutaraldehyde process is only one processing method, however, and a scaffold material processed according to any other method as is known in the art may alternatively be utilized. For example, a scaffold material as may be utilized in a disclosed composite implant can be stabilized according to a physical crosslinking process including, without limitation, chemical treatment, radiation treatment, thermal treatment, electron beam treatment, UV crosslinking, and the like.

In one preferred embodiment, a scaffold can be processed according to a non-glutaraldehyde crosslinking process. For example, non-glutaraldehyde crosslinking methods as disclosed in U.S. Pat. Nos. 5,447,536 and 5,733,339 to Girardot, et al., both of which are incorporated herein by reference, can be utilized. According to one such embodiment, a collagen-containing scaffold can be crosslinked via formation of amide linkages between and within the molecules of the scaffold. For instance, di- or tri-carboxylic acids and di- or tri-amines of about six to eight carbon atoms in length can be used in a sequential manner to form amide crosslinks.

A scaffold 25 can be affixed to an elongated member 28 along at least a portion of the length of the scaffold 25. In particular, a scaffold 25 can be affixed to an elongated member 28 in such a fashion that elongated member 28 can bring desirable characteristics to the approximation device 26 including one or more mechanical characteristics such as strength, tenacity, load distribution and maneuverability.

Beneficially, an elongated member 28 can be affixed to a scaffold 25 so as to provide a means for manipulating and locating a scaffold 25 in desired relation to fixation device 10.

In one preferred embodiment, an elongated member 28 can be suture, but this is not a requirement of an approximation device 26. Other suitable materials for use as elongated member 28 can include, e.g., polymer fabrics, elongated members derived from natural tissues such as ligaments and tendons, and the like.

The components of approximation device 26 can be held together in any fashion. For instance, an elongated member 28 and a scaffold 25 can be stitched together, interwoven, braided together, twisted together, clipped together, secured with a bioadhesives, or any combination of techniques.

An approximation device 26 can include additional materials as well. For instance, an approximation device 26 can include biologically active materials such as growth factors, antibiotics, living cells, etc., as well as structural materials including anchoring materials, additional scaffolds, additional implants, and so on.

Figure 9:
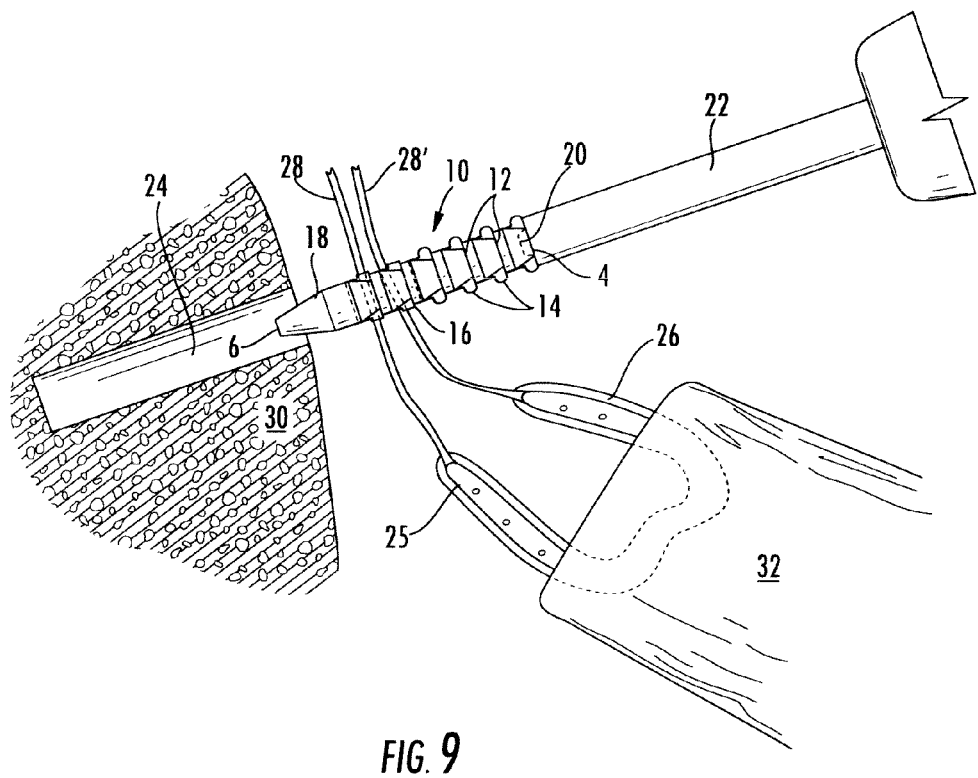
FIG. 9 illustrates one embodiment of a method of utilizing a fixation device as disclosed herein to approximate a damaged soft tissue to a bony insertion site.

Disclosed methods are not limited to utilization of approximation devices such as those illustrated in FIG. 9. In another embodiment, disclosed fixation devices can be utilized in conjunction with approximation devices as disclosed in U.S. patent application Ser. No. 12/205,260 to Brunelle, et al., incorporated herein by reference. For example, FIGS. 15A and 15B illustrate another embodiment of an approximation device 126 as may be utilized in disclosed methods. As can be seen, a portion of approximation device 126 defines a width W that can be greater than that of standard suture. For instance W can be greater than about 1 millimeter (mm).

Approximation device 126 can be a tissue repair construct comprising a mechanical reinforcing component 127 combined with a cellular scaffold component 125 attached to the wider central region of the reinforcing component 127 on one or, as in the illustrated embodiment, on both sides of the reinforcing component 127. In this illustrated embodiment, the reinforcing component 127 is a woven construct that tapers to a narrow extension 128, 128' on either end of the wider portion of the reinforcing component 127. Device 126 can function, for example, as a surgical mesh to repair soft tissue while providing excellent mechanical support to the repair (e.g. repair of soft tissue to bone).

The reinforcing component 127 of approximation device 126 can be formed from any of a wide variety of biocompatible materials, as well as combinations of materials. For instance, reinforcing component 127 can be formed from any of a wide variety of biocompatible substituted or unsubstituted polymeric materials including, without limitation, polyketones such as polyether ether ketone; polyesters such as high tenacity polyester; polyethylene such as ultra high molecular weight polyethylene; absorbable polymers including those based upon polylactic acid and/or polyglycolic acid; natural polymers such as silk; biologic materials such as collagen; and the like. Reinforcing component 127 can also be formed from any of a wide variety of metallic materials, including, without limitation, stainless steel, titanium, and the like.

In one embodiment, the reinforcing component 127 of approximation device 126 can include fibrous materials such as mono- or multi-filament fibers or yarns that can be absorbable or non-absorbable and can define any cross-sectional area. For instance, the reinforcing component 127 of approximation device 126 can be a woven, nonwoven, or knit fabric and can define a porosity throughout all or a portion of reinforcing component 127 and can be formed to describe a predetermined tensile strength. For instance, reinforcing component 127 can describe a tensile strength of at least about 20N.

As previously mentioned, reinforcing component 127 can taper at either end of the wider portion to form extensions 128, 128' that can facilitate delivery and/or placement of the approximation device 126 in conjunction with a fixation device as disclosed herein. In addition, extensions 128, 128' can be of any suitable cross sectional geometry, e.g., flat, round, square, tubular, etc.

The relationship in width between a wide portion of a reinforcing component 127 and extensions 128, 128' can be as desired. For instance, extensions 128, 128' can be the same or different from one another and can be less than about 90%, less than about 60%, less than about 50%, or less than about 30% of a wider portion of reinforcing component 127.

In addition, an approximation device can have multiple portions of varying width. For example, an approximation device can include two or more wide portions separated by narrower, elongated sections.

In one embodiment, the cellular scaffold component 125 of approximation device 126 can include a collagen scaffold, a hydrogel scaffold, or a natural soft tissue affixed to the approximation device, for instance sewn to the surface of the wide portion of the device 126.

Referring again to FIG. 9, in utilizing a fixation device 10 as disclosed herein, a soft tissue or an approximation device 26, e.g., those specifically described above or any other suitable approximation device known to those of skill in the art, including suture, can be passed through transverse aperture 16. For example, as illustrated in FIG. 9, an approximation device 26 can be applied to a tissue 32, e.g., a tendon, and inserted across the transverse aperture 16. If necessary, approximation device 26 can be trimmed to fit across transverse aperture. For instance, in those embodiments in which approximation device includes a cellular scaffold, it may be desirous to trim a scaffold 25 to fit into or through transverse aperture 16.

In those embodiments in which an endogenous tissue or tissue graft is directly affixed to a fixation device, without the addition of an approximation device between the two, the tissue can be prepared for attachment to a bony insertion site in standard fashion via debridement, mobilization, etc. Following any preparation, the tissue can be shaped as necessary so as to fit at least a portion of the tissue through the transverse aperture 16.

Fixation device 10 can be attached to driver 22 at the threaded inset 20 and can be lined up with the preformed bone hole 24. Bone hole 24 can be formed according to known methods (e.g., utilization of a bone tap according to known practices) to a size and shape for use with disclosed devices. For example, bone hole 24 can be round or oval, and can include a first axis that is slightly less than the longer aspect of device 10 and a second axis that is about equivalent to the shorter aspect of device 10. Accordingly, the sharp edged ribs 12 can hold device 10 tightly within bone hole, and the round ridged ribs 14 can hold a soft tissue or a portion of an approximation device within bone hole via the atraumatic, rounded ridges of ribs 14. Device 10 can be driven into the bone hole 24 until seated such that proximal end 4 of fixation device 10 is about even with the surface of bone 30 or optionally just below the surface of bone 30, for instance should a cortical layer exist.

Beneficially, fixation device 10 can be seated in bone hole 24 with direct, axial delivery of the device, which can provide for simple delivery of the device 10 and soft tissue to the surrounding bone. In addition, axial delivery, particularly when combined with tapering of the end of the device so as to provide small distal end 6, can provide for proper alignment of both the device and associated tissues, as well as reducing the potential for deviation of associated tissue from the intended placement point during a procedure.

Figure 10:
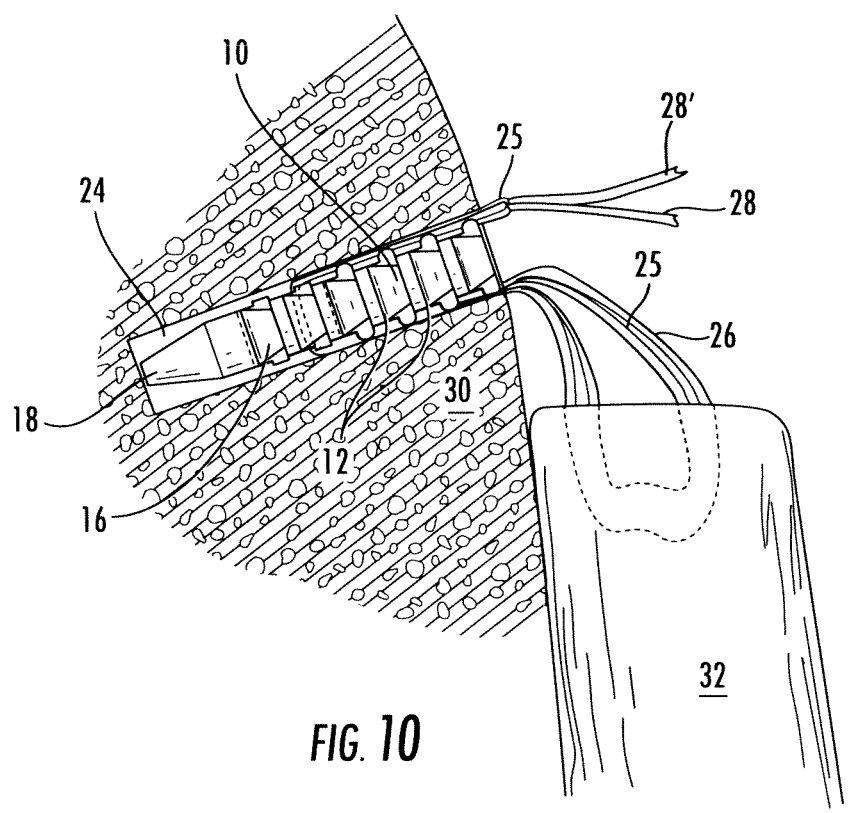
FIG. 10 illustrates a fixation device as disclosed herein following insertion in a bone hole.

FIG. 10 illustrates device 10 following insertion into bone 30. As can be seen, scaffold 25 of device 26 extends on either side of device 10, and specifically, the sides of device including ribs 14 that define rounded, atraumatic ridges. Scaffold 25 also extends through transverse aperture 16. Following insertion, ribs 12 defining sharp edges, can tightly hold device 10 within bone hole 24, while ribs 14 can hold approximation device 26 within bone hole 24 without damage to approximation device 26. For example, a device as disclosed herein can exhibit a pull out resistance force at time 0 (i.e., immediately following insertion) that is appropriate in comparison to similar bone interfacing devices.

In addition, the presence of a cellular scaffold 25 within bone hole 24 can encourage cellular growth and development at the walls of the fixation device 10 as well as through the transverse aperture 16 over time. Similarly, the presence of endogenous or transplanted tissue within bone hole 24 and transverse aperture 16 in those embodiments in which these tissues are directly affixed to a device can encourage healing and cellular development between the tissue and the surrounding bone.

Referring to FIGS. 11A-11D, a fixation device 10 can be utilized to directly affix a tissue 32, e.g., a tissue graft formed of a natural or synthetic tissue or a damaged endogenous tissue, directly to a bone 30. Due to beneficial aspects of the disclosed devices, implantable tissue grafts, e.g., synthetic or natural tissues as may be utilized for transplants, or damaged endogenous tissues, e.g., a tendon stump, can be directly associated with a fixation device as disclosed herein and affixed within a bone tunnel or bone slot. More specifically, in this particular embodiment, a tissue 32 can be directly affixed to the bone 30.

Figure 11A:
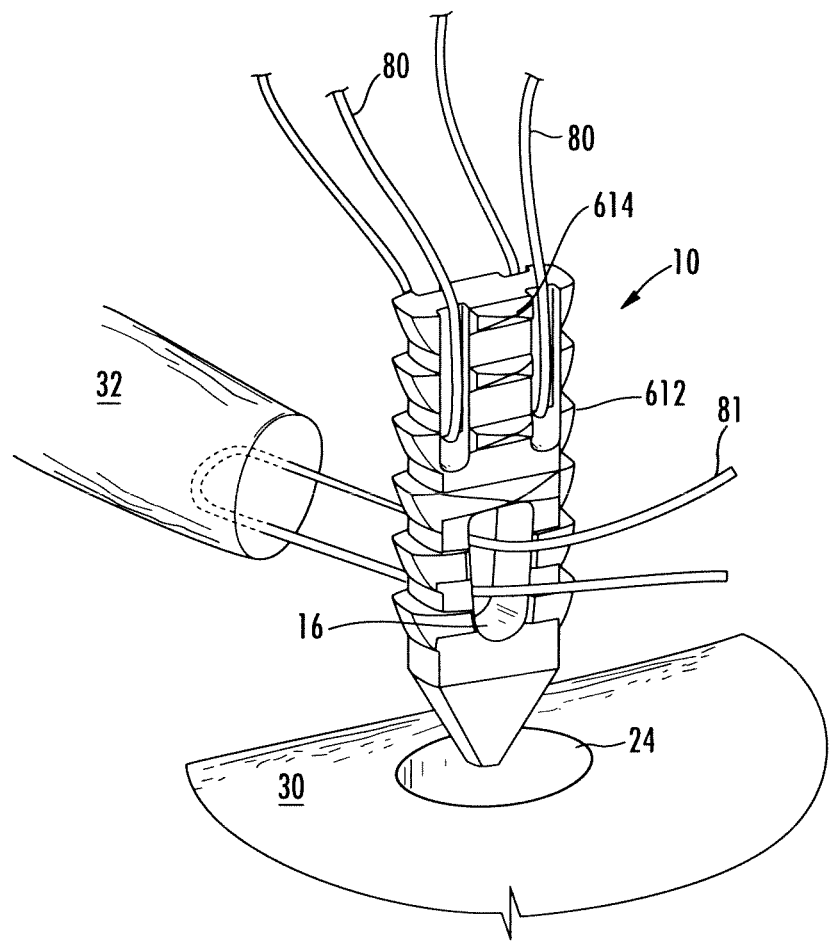
FIGS. 11A-11D illustrate one embodiment of a method of utilizing a fixation device as disclosed herein for fixation of a tendon stump.
Figure 11B:
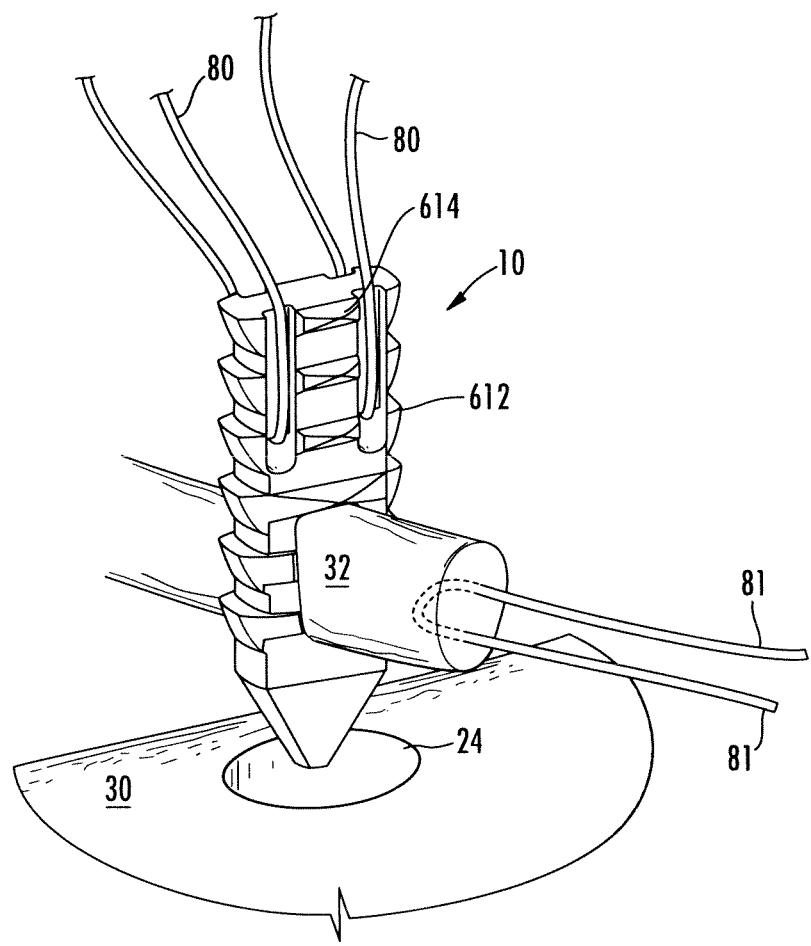
Figure 11C:
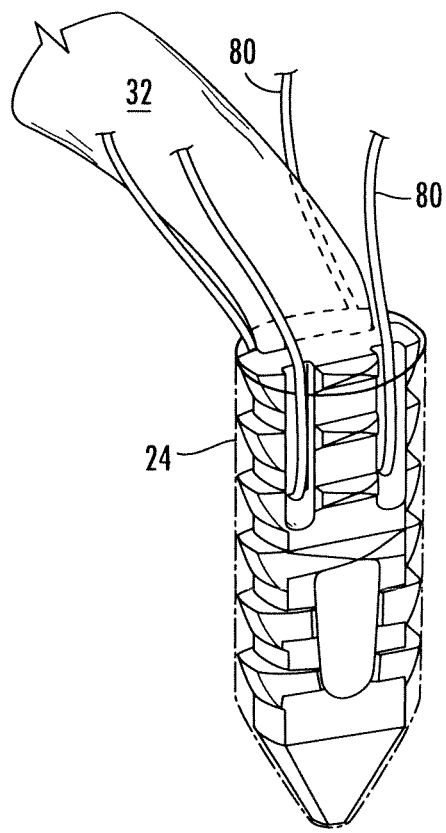
Figure 11D:
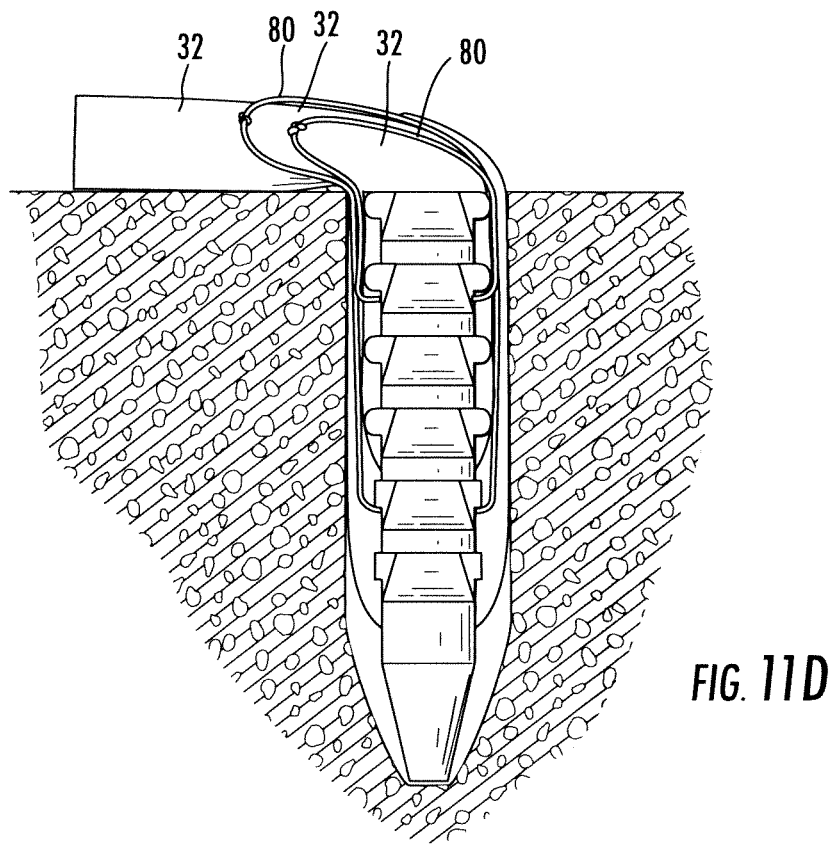

FIGS. 11A-11D illustrate one example of this technique. Initially, an approximation device (e.g. suture 81) is attached to a tendon stump 32, for instance in a whipstitch fashion. The tendon stump 32 is then passed through the transverse aperture 16 such that tissue 32 is in contact with each opposing portion of the device 10 that defines rounded ribs 614 (FIGS. 11A-11B). The device 10 is then delivered to a bone hole as described previously (FIG. 11C). In this particular embodiment, the device 10 also includes attached sutures 80 (described above with reference to FIG. 8) that can be used for additional fixation of the soft tissue near the bone tunnel entrance (FIG. 11D, shown in cross section).

Figure 12:
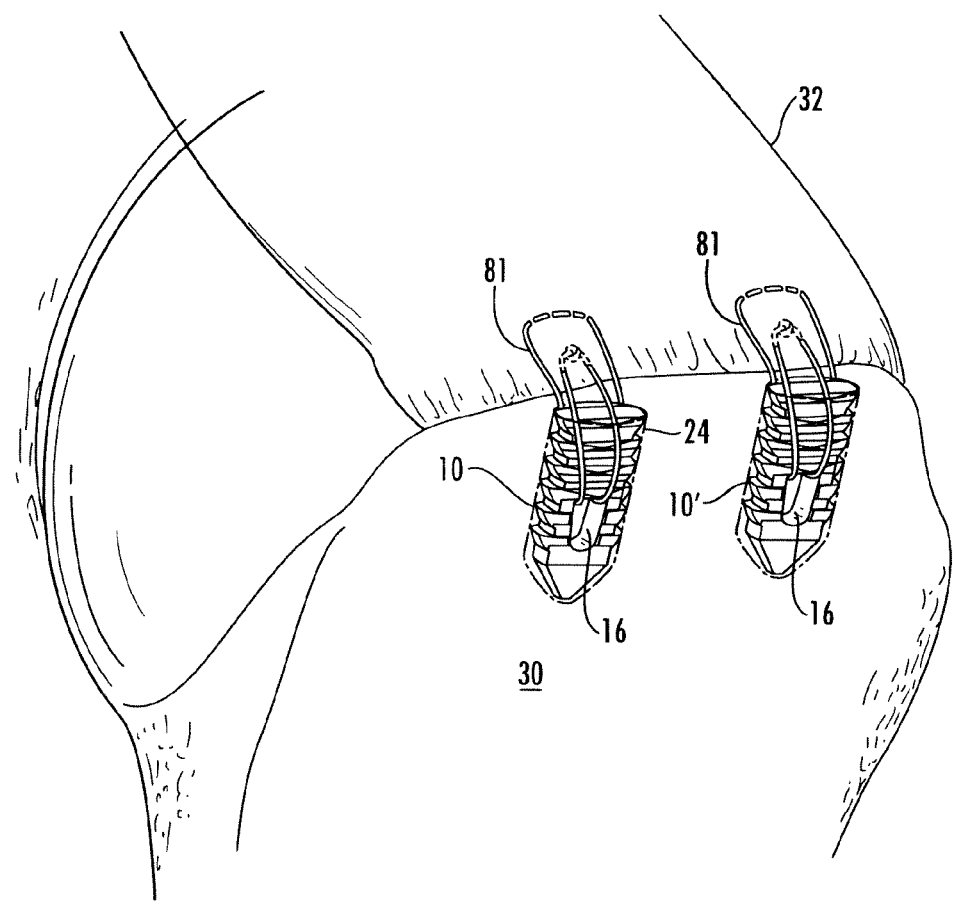
FIG. 12 illustrates one embodiment of a rotator cuff repair method utilizing a fixation device as disclosed herein.

FIG. 12 illustrates a single row rotator cuff repair using two substantially identical fixation devices 10 used in conjunction with sutures 81 that have been delivered to the tendon in an inclined mattress configuration. Specifically, a suture 81 can pass through the tendon with a mattress stitch, through transverse aperture 16 such that upon delivery of the device 10 into the bone hole 24 of the bone 30, the suture 81 can be located between device 10 and the surrounding bone tissue within the hole 24. Optionally, the two ends of suture 81 can be again passed through tendon stump 32 and tied off according to known methods. The use of a mattress stitch, though not required, can enhance the strength of the suture to tendon interface, and the disclosed device provides a functional means for subsequent fixation of the suture strands to bone, specifically during arthroscopic repair.

Figure 13:
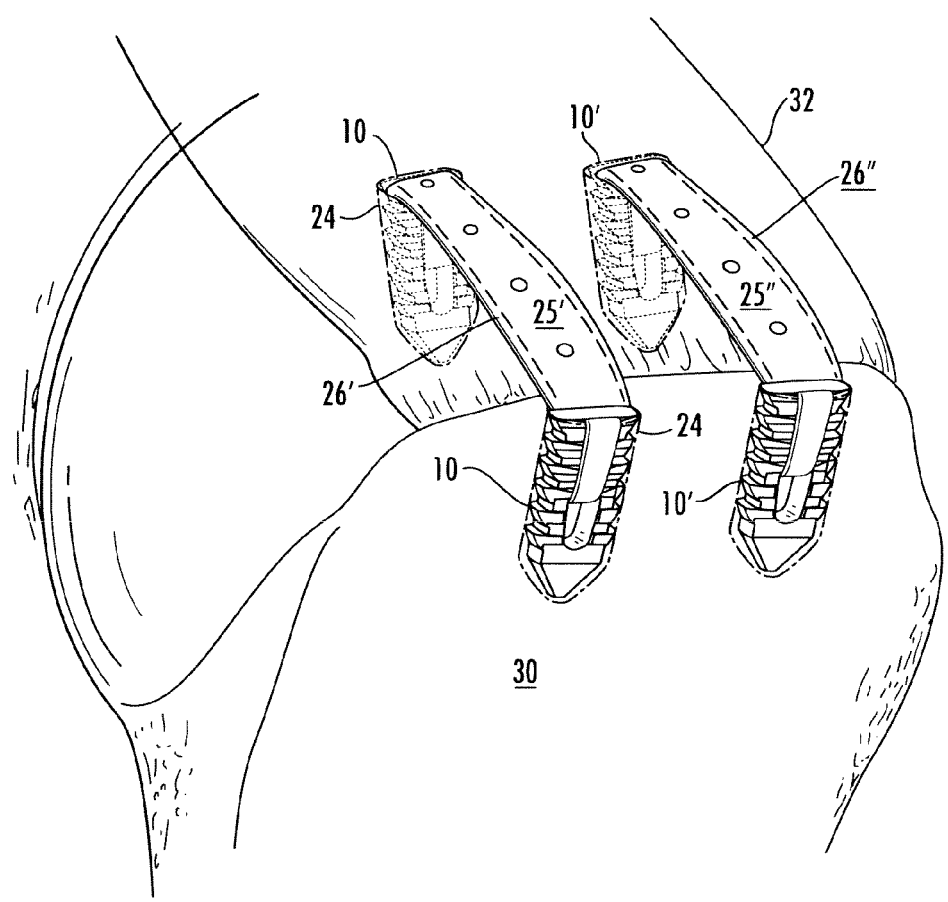
FIG. 13 illustrates another embodiment of a rotator cuff repair method utilizing a fixation device as disclosed herein.

FIG. 13 illustrates a double row rotator cuff repair using four fixation devices 10 as disclosed herein in conjunction with two approximation devices 26', 26". The approximation devices 26', 26" are generally wider than suture and include a cellular scaffold 25', 25", and can function in part as surgical mesh. In this embodiment, a first approximation device 26' can be fixated on the medial aspect of the boney insertion site 30 though a pre-formed hole 24 using a device 10 as describe previously either anterior or posterior to the midline of the defect such that a portion of cellular scaffold 25' is in contact with the bone hole 24 and between device 10 and the surrounding tissue within bone hole 24. A second approximation device 26" is fixated in the same manner using a second fixation device 10' anterior to the midline of the defect. The approximation devices 26', 26" are then shuttled through the tissue 32 using standard tendon passing methods and pulled laterally such that the tendon stump 32 maintains intimate contact with the boney insertion site 30. The opposing ends of the approximation devices 26', 26" are then separately fixated laterally though additional pre-formed bone holes using additional fixation devices 10 using appropriate tension. This particular embodiment can allow for enhanced pressure distribution and contact area at the tendon/bone interface forming a beneficial healing environment.

Figure 14:
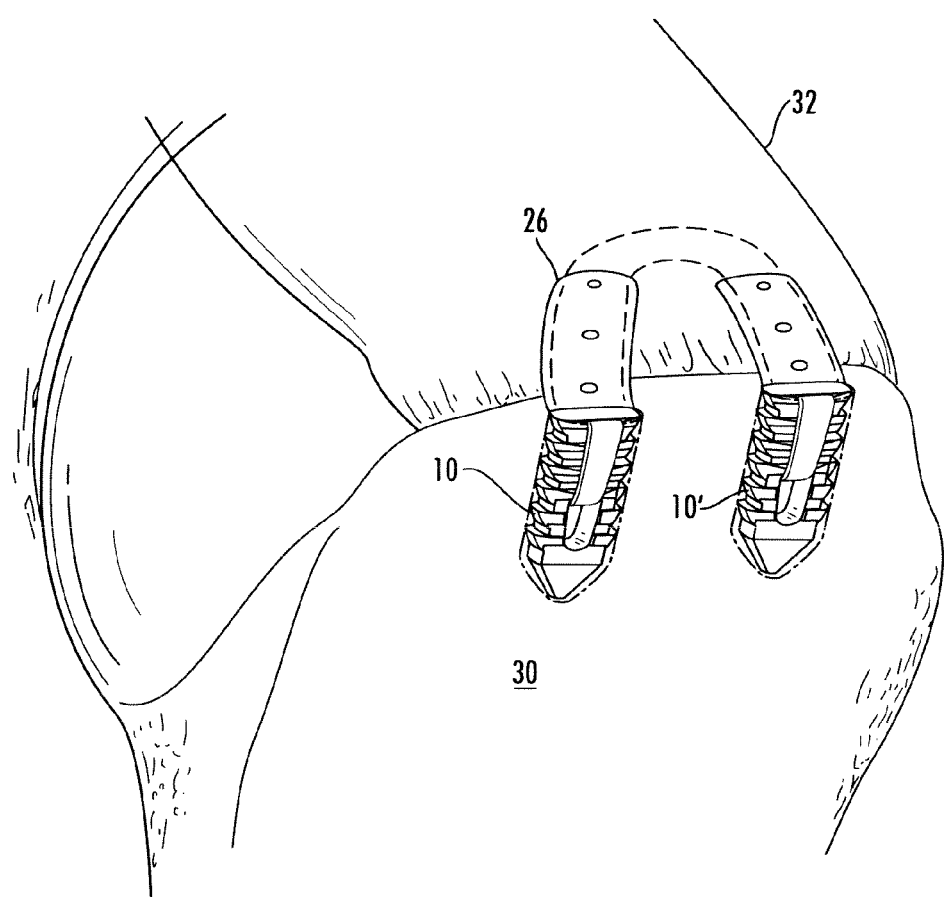
FIG. 14 illustrates another embodiment of a rotator cuff repair method utilizing a fixation device as disclosed herein.

FIG. 14 illustrates a rotator cuff repair using two fixation devices 10, 10' disclosed herein in conjunction with one approximation device 26. In this method, the approximation device 26 can be applied to the tendon in an inclined mattress stitch configuration with opposing ends of the approximation device 26 fixated separately using two fixation devices 10, 10' along the lateral aspect of the boney insertion site. This technique can provide benefits with regard to ease of use, repair, and enhanced strength of the suture to tendon interface, specifically during arthroscopic repair.

It will be appreciated that the foregoing embodiments, given for purposes of illustration, are not to be construed as limiting the scope of this disclosure. Although only a few exemplary embodiments have been described in detail above, those skilled in the art will readily appreciate that many modifications are possible in the exemplary embodiments without materially departing from the novel teachings and advantages of this disclosure. Accordingly, all such modifications are intended to be included within the scope of the following claims and all equivalents thereto. Further, it is recognized that many embodiments may be conceived that do not achieve all of the advantages of some embodiments, yet the absence of a particular advantage shall not be construed to necessarily mean that such an embodiment is outside the scope of the present disclosure.

What is claimed is:

1. A tissue fixation device comprising
a proximal end and a distal end and defining a longitudinal axis from the proximal end to the distal end, the tissue fixation device further defining
a first cross sectional area along at least a portion of and perpendicular to the longitudinal axis, the first cross sectional area defining
a periphery and including a first aspect having a first length and a second aspect that is perpendicular to the first aspect and having a second length,
wherein the first length is greater than the second length such that the cross sectional area is oblong; and further comprising
a first rib extending from a first portion of the periphery of the first cross sectional area, the first portion of the periphery including a terminus of the first aspect, wherein the first rib defines a sharp edge, the device also comprising
a second rib distinct from the first rib and in a same cross sectional plane of the device as the first rib and extending from a second portion of the periphery of the first cross sectional area, the second portion of the periphery including a terminus of the second aspect, wherein the second rib defines a rounded ridge.

2. The tissue fixation device according to claim 1, wherein the sharp edge is oriented toward the proximal end of the device.

3. The tissue fixation device according to claim 1, further defining a transverse aperture through the device, the transverse aperture being generally perpendicular to the longitudinal axis of the tissue fixation device.

4. The tissue fixation device according to claim 3, wherein the transverse aperture is aligned with the second aspect of the first cross sectional area.

5. The tissue fixation device according to claim 3, wherein a distance from a center of the transverse aperture to the distal end is less than a distance from the center of the transverse aperture to the proximal end.

6. The tissue fixation device according to claim 3, wherein the transverse aperture is circular, ovoid, triangular or elliptical.

7. The tissue fixation device according to claim 1, wherein the distal end defines a second cross sectional area that is smaller than the first cross sectional area.

8. The tissue fixation device according to claim 1, wherein the tissue fixation device is between about 5 millimeters and about 30 millimeters in length as measured from the proximal end to the distal end.

9. The tissue fixation device according to claim 1, wherein the first length is between about 2 millimeters and about 10 millimeters.

10. The tissue fixation device according to claim 1, wherein the second length is between about 1 millimeter and about 6 millimeters.

11. The tissue fixation device according to claim 1, further defining an inset in the proximal end configured to interface with a delivery mechanism.

12. The tissue fixation device according to claim 11, where in the inset is threaded.

13. The tissue fixation device according to claim 1, further defining a protrusion in the proximal end configured to interface with a delivery mechanism.

14. The tissue fixation device according to claim 1, wherein the tissue fixation device is sterile.

15. The tissue fixation device according to claim 1, wherein the first cross sectional area is an ellipse.

16. The tissue fixation device according to claim 1, wherein the first cross sectional area is a rectangle.

17. The tissue fixation device according to claim 1, further comprising two or more apertures that are generally perpendicular to the longitudinal axis.

18. The tissue fixation device according to claim 17, wherein the apertures are parallel with one another.

19. The tissue fixation device according to claim 17, wherein the apertures are aligned with the shorter aspect of the oblong cross sectional area of the device.

20. The tissue fixation device according to claim 17, further comprising grooves that are aligned parallel to the longitudinal axis and extend from the apertures to the proximal end of the device.

21. The tissue fixation device according to claim 1, wherein at least a portion of the cross sectional area of the device tapers with respect to the longitudinal axis from the proximal to the distal end.

22. The tissue fixation device according to claim 1 in combination with a tissue approximation device, the tissue approximation device comprising a mechanical reinforcing component and a cellular scaffold component.

23. The tissue fixation device according to claim 1, wherein the first cross sectional area is an ovoid.

24. The tissue fixation device according to claim 1, comprising more than one rib defining a sharp edge and more than one rib defining a rounded ridge.

25. The tissue fixation device according to claim 24, wherein the number of ribs defining a sharp edge is different than the number of ribs defining a rounded ridge.

26. The tissue fixation device according to claim 24, comprising an equal number of ribs defining a sharp edge on two opposing portions of the device and an equal number of ribs defining a rounded ridge on two opposing portions of the device.

* * * * *